(12) United States Patent
Pohl et al.

(10) Patent No.: US 9,400,268 B2
(45) Date of Patent: Jul. 26, 2016

(54) METHOD FOR REDUCING SUPPRESSOR NOISE

(71) Applicant: DIONEX CORPORATION, Sunnyvale, CA (US)

(72) Inventors: Christopher A. Pohl, Union City, CA (US); Kannan Srinivasan, Tracy, CA (US); Brittany Omphroy, San Jose, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 0 days.

(21) Appl. No.: 14/455,710

(22) Filed: Aug. 8, 2014

(65) Prior Publication Data

US 2016/0041133 A1  Feb. 11, 2016

(51) Int. Cl.
*G01N 30/96* (2006.01)
*B01D 15/36* (2006.01)

(52) U.S. Cl.
CPC .............. *G01N 30/96* (2013.01); *B01D 15/361* (2013.01); *G01N 2030/965* (2013.01)

(58) Field of Classification Search
CPC . G01N 30/96; G01N 2030/965; B01D 15/361
See application file for complete search history.

(56) References Cited

U.S. PATENT DOCUMENTS

| | | | |
|---|---|---|---|
| 4,265,634 A | 5/1981 | Pohl | |
| 4,999,098 A | 3/1991 | Pohl et al. | |
| 5,248,426 A | 9/1993 | Stillian et al. | |
| 5,352,360 A | 10/1994 | Stillian et al. | |
| 5,569,365 A | 10/1996 | Rabin et al. | |
| 5,597,481 A | 1/1997 | Stillian et al. | |
| 5,597,734 A | 1/1997 | Small et al. | |
| 5,773,615 A | 6/1998 | Small et al. | |
| 6,077,434 A * | 6/2000 | Srinivasan | G01N 30/96 204/520 |
| 6,325,976 B1 | 12/2001 | Small et al. | |
| 6,328,885 B1 | 12/2001 | Srinivasan et al. | |
| 6,425,284 B1 | 7/2002 | Srinivasan et al. | |
| 6,436,719 B1 | 8/2002 | Srinivasan et al. | |
| 6,495,371 B2 | 12/2002 | Small et al. | |

(Continued)

FOREIGN PATENT DOCUMENTS

| | | |
|---|---|---|
| CN | 1403811 | 3/2003 |
| CN | 1744945 | 3/2006 |

OTHER PUBLICATIONS

Douglas et al., "New suppressor technology improve trace level anion analysis with carbonate-hydrogencarbonate mobile phases," J Chrom A, 956, 2002, 47-51.

(Continued)

*Primary Examiner* — Arun S Phasge
(74) *Attorney, Agent, or Firm* — Jeffry S. Mann (57) ABSTRACT

An electrolytic method for suppressing liquid eluent containing previously separated sample analyte anions, counterions to the sample anions, and non-sample anions suppressible to weak acids in an electrolytic device comprising a housing defining at least a sample stream flow channel and an ion receiving flow-through channel separated by an ion exchange bather. The sample stream flow channel includes an upstream channel portion and a downstream channel portion. A first current is applied across the upstream channel portion for substantially completely suppression. A second current is applied across the downstream channel portion at a magnitude of less than 10% of the magnitude of the first current.

7 Claims, 8 Drawing Sheets

(56) References Cited

U.S. PATENT DOCUMENTS

| | | |
|---|---|---|
| 6,508,985 B2 | 1/2003 | Small et al. |
| 6,610,546 B1 | 8/2003 | Liu et al. |
| 7,399,415 B2 | 7/2008 | Srinivasan et al. |
| 7,517,696 B2 | 4/2009 | Srinivasan et al. |
| 7,524,457 B2 | 4/2009 | Srinivasan et al. |
| 8,415,168 B2 | 4/2013 | Liu et al. |
| 2005/0034997 A1 | 2/2005 | DiMascio et al. |
| 2006/0254969 A1 | 11/2006 | Yamanaka et al. |
| 2007/0051684 A1 | 3/2007 | Grebenyuk et al. |
| 2009/0127200 A1 | 5/2009 | Dasgupta et al. |
| 2009/0308757 A1 | 12/2009 | Crettenand |
| 2013/0306565 A1 | 11/2013 | Davis |

OTHER PUBLICATIONS

Saari-Nordhaus et al., "Recent advances in ion chromatography suppressor improve anion separation and detection," J Chrom A, 956, 2002, 15-22.

Srinivasan et a., "Suppressor Design and Detection for Ion Chromatography" in: "Applications of Ion Chromatography for Pharmaceutical and Biological Products," Mar. 9, 2012, John Wiley & Sons, Inc., pp. 91-105.

U.S. Appl. No. 13/674,738, filed Nov. 12, 2012, to Srinivasan (specification, claims, abstract only).

* cited by examiner

METHOD FOR REDUCING SUPPRESSOR NOISE

BACKGROUND OF THE INVENTION

The use of a continuously regenerated electrolytic membrane suppressor in ion analysis is well established. The primary function of a suppressor is to lower the background by converting chromatography eluent to a weakly dissociated form while converting fully dissociated sample analyte ions to a conductive form. Historically, there have been significant efforts dedicated to lowering the chromatographic noise of suppressor devices. The primary contributors of noise are a) suppressor background, b) leachate levels c) operational parameters such as current, temperature etc. These development efforts aided improved noise performance, particularly with eluents such as potassium hydroxide, sodium hydroxide, methanesulfonic acid etc. With eluents that were carbonate and/or bicarbonate based, the suppressed eluent was carbonic acid and resulted in higher noise relative to when the suppressed eluent was deionized water. One solution to the high noise issue has been to pass the suppressed eluent through a post suppressor carbonate removal device that removed the dissolved carbon dioxide from the carbonic acid effluent, thus lowering the background and achieving low noise.

Current-efficient electrolytic suppressors are described in U.S. Pat. No. 6,077,434 (the "'434 patent"). The structure of such suppressors may be a two-channel device with a sample stream flow channel separated from an ion receiving flow channel by an anion exchange barrier which passes eluent counterions to the analyte ions during suppression. Also, a three-channel sandwich-type suppressor is disclosed in which the sample stream flow channel is separated from flanking ion receiving channels by two ion exchange barriers. The upstream portion of the sample stream flow channel has lower electrical resistance than the downstream portion. The '434 patent discloses (at column 17, line 10 through column 18, line 7) a number of ways to accomplish this including the use of a first pair of electrodes for the upstream portion and another electrode pair for the downstream portion. Independent power sources for the electrode pairs or the use of a resistor in the downstream portion of the electrodes are disclosed as ways to lower the resistance in the downstream portion. At column 13, line 55 through column 14, line 11, the patent teaches that, if the sample stream flow channel is packed with ion exchange medium, it should be of low capacity.

SUMMARY

In accordance with the invention, an electrolytic method is provided for suppressing liquid eluent containing previously separated sample analyte anions, counterions to said sample analyte ions, and non-sample anions suppressible to weak acids. The method is performed in an electrolytic device comprising (a) a housing defining at least a sample stream flow channel and an ion receiving flow-through channel, the sample stream flow channel being adjacent to the ion receiving flow channel; (b) a first ion exchange barrier which permits ion transport and blocks bulk liquid flow disposed between the sample stream flow channel and the ion receiving flow channel, the sample stream flow channel including an upstream channel portion and a downstream channel portion; and (c) high capacity ion exchange medium disposed in the downstream channel portion. The method comprises (a) applying a first current across the upstream channel portion to substantially completely suppress the counterions and to convert the non-sample anions to weak acids in the upstream channel portion by transport of the counterions across the first ion exchange barrier; and (b) applying a second current across the downstream channel portion to substantially reduce the noise of the weak acids during subsequent detection, the second current being at a magnitude of less than 10% of the magnitude of said first current.

DETAILED DESCRIPTION OF EMBODIMENTS

The system of the present invention is useful for determining a large number of anions. Suitable samples include surface waters and other liquids such as industrial chemical waste, body fluids, beverages such as fruits, wines and drinking water.

The present invention is directed to a method for treating an aqueous sample stream including analyte anions and counter ions of opposite charge (cations). The treatment is in a suppressor for ion chromatography and the counter ions are the electrolyte cations in the eluent of opposite charge to the analyte ions.

The present invention is directed to the reduction of noise from suppressed suppressible weak acid anions present in the eluent prior to mixing with the sample analytes (termed "non-sample anions"). Thus, prior to mixing with the sample anions, the eluent may include a cation (e.g. potassium or sodium) salt of a weak acid non-sample anion (e.g. carbonate, bicarbonate, or borate). As will be explained, the cation, which is a counter ion to the anionic analytes, is removed during suppression by transport across an ion exchange bather to leave the suppressible non-sample weak anion in acid form, producing noise during detection which is reduced by the method of the present invention. The noise reduction and consequent signal to noise improvement can be as high as a 10 fold regime.

In general, unless otherwise specified, the principles and details of the suppression methods of the present invention and suitable apparatus for performing the methods are as described in the '434 patent, incorporated by reference. Both the '434 patent and the present invention relate to an electrolytic suppression method in which the upstream portion of the sample flow channel has greater current applied than the downstream portion.

As described, according to the present invention suppression of the counter ions is complete or substantially complete in the upstream portion before flow of the sample stream to the downstream portion. "Substantially complete" suppression is defined to mean that the current applied to the upstream portion is adequate to achieve complete suppression which is defined as removal of the sample and eluent counterions, cations in the anion analysis case, to greater than 99%, preferably greater than 99.5% and more preferably greater than 99.9%. No additional treatment is required to achieve suppression.

In contrast to the '434 patent, high capacity ion exchange medium is disposed in the downstream portion of sample stream flow channel. "High capacity" is defined for an operational flow rate of 1 ml/min as a minimum of 0.01 meqv, preferably greater than 0.02 meqv, and more preferably greater than 0.03 meqv. Advantages of using high capacity medium in the downstream portion include high static capacity that allows operation of the suppressor without any applied power. Further the high capacity allows analysis of samples containing high matrix concentrations. The high capacity overall provides a reservoir of static capacity that makes the device user friendly and results in continuous operation of the device with no down time. Thus high capacity provides significant ease of use.

The high capacity medium in the downstream portion can be of similar high capacity to ion exchange medium in the ion receiving flow channel on the opposite side of the ion exchange barrier. Suitable forms of ion exchange media are described in the '434 patent such as screens, packed beds of ion exchange particles, and flow-through ion exchange monoliths.

Suitable electrolytic suppressors according to the invention are described in the '434 patent, including (a) a two-channel suppressor with a sample stream flow channel separated from an ion-receiving flow channel by an ion exchange barrier or (b) a sandwich suppressor with two ion receiving channels flanking and separated from the sample stream flow channel by two barriers.

The difference in the magnitude of the currents applied in the upstream and downstream portions of the sample flow channel may be controlled as in the devices described at column 17, line 10 to column 18, line 7 of the '434 patent.

As defined herein, the "upstream portion" of the sample flow channel is the sample flow channel portion at the inlet side disposed between first spaced electrodes or electrode portions that supply a first higher current across the sample flow channel for substantially complete suppression.

The "downstream portion" of the sample stream flow channel is the sample flow channel at the outlet side disposed between second spaced electrodes or electrode portions that supply a second lower current across the sample flow channel than the upstream portion.

Suitable devices to apply such currents include the ones described in the '434 patent at column 17 and 18 including the following: (a) using a first electrode spaced pair adjacent the upstream portion and a second spaced electrode pair adjacent the downstream portion; in which each electrode pair is connected to a separate power source; or (b) using a single power source for all electrodes in which the second electrode pair is connected to a resistance (resistor) in series but the first pair is not connected to one. Also, one of the electrodes in the second electrodes assembly in the downstream portion connected to a resistor may be spaced from an electrode in the upstream portion while the electrode assembly on the opposite side the sample stream flow channel is continuous and may or may not be connected to a resistor. Some of these embodiments of suitable electrode configurations will be described in more detail.

By way of background, it is known that the suppressor current influences the noise performance of the suppressor. Application of currents higher than the current required for suppression leads to higher noise therefore it is best to operate near the optimal regime. The current needed to suppress a given eluent using a 100% current efficient device can be calculated based on Faraday's equation.

$$i_{100} = \frac{f\ cv}{60} \quad (1)$$

where
  $i_{100}$ is the current in mA for a device with 100% current efficiency
  f is Faraday's constant
  c is the concentration in M
  v is the flow rate in mL/min For example, for suppressing an eluent comprising of 20 mM potassium hydroxide, the above equation calculates the required current to be approximately 32 mA. It is also known that if the current applied is higher than what is required for suppression for a given suppressor, the noise increases and the wattage increases. Maintaining a high current efficiency is important, as this ensures that the suppressor draws the current required for suppression.

It has been discovered according to the present invention that, despite operating with currents at the current efficient regime, there is a residual background after suppression that is highly influenced by the applied current on a suppressor. This residual background fluctuates, resulting in high noise, particularly when the suppressed effluent is weakly dissociated and is conductive, such as with carbonic acid background. In the case of a potassium hydroxide eluent that is generated with an eluent generator, the background is deionized water and is unaffected since it is substantially nonconductive and any fluctuations do not translate into high noise. This is the reason the suppressors of the prior art are capable of achieving low noise with eluents that result in the formation of deionized water as the suppression product.

For eluents that result in weakly dissociated species that are conductive such as carbonic acid, substantially higher noise is observed. For example, the typical noise with carbonate and or bicarbonate eluents is in the 3 to 10 nS/cm regime.

According to the present invention, lowering the current at the outlet of the suppressor resulted in minimal background fluctuation and thus resulted in low noise with carbonate and/or bicarbonate eluents. Lower current applied in the sample stream channel downstream portion does not significantly affect the substantially complete suppression in the upstream portion. It is believed that the application of a low current minimizes transport of neutral components of the weakly dissociated species across the sample stream flow channel of the suppressor. The ionic species in the sample stream flow channel cannot be transported across the membrane due to the repulsion forces from the charged membrane. The ion exchange membrane is called a donnan barrier and like charges are repelled due to the donnan potential which is a potential that develops based on the net charge on the membrane. For example during anion analysis the membrane carries anionic charges from sulfonated moieties on the membrane. The carbonic acid background comprises of bicarbonate anion which is repelled by the sulfonated anionic charges on the membrane. However, the membrane cannot reject neutral carbonic acid species which can freely travel across the membrane. Thus, carbonic acid, which is conductive, can be transported across the membrane causing variations in the observed background signals.

According to the present invention, the transport of the neutral species is higher at higher currents leading to higher variations in the observed background that leads to substantial noise. Lowering the current ensures that the transport of the weakly dissociated neutral species is minimized thus leading to lower noise. By separating the suppression function from the noise function according to the present invention provides a practical solution to the noise issue with carbonate and/or bicarbonate eluents.

Figure 1:
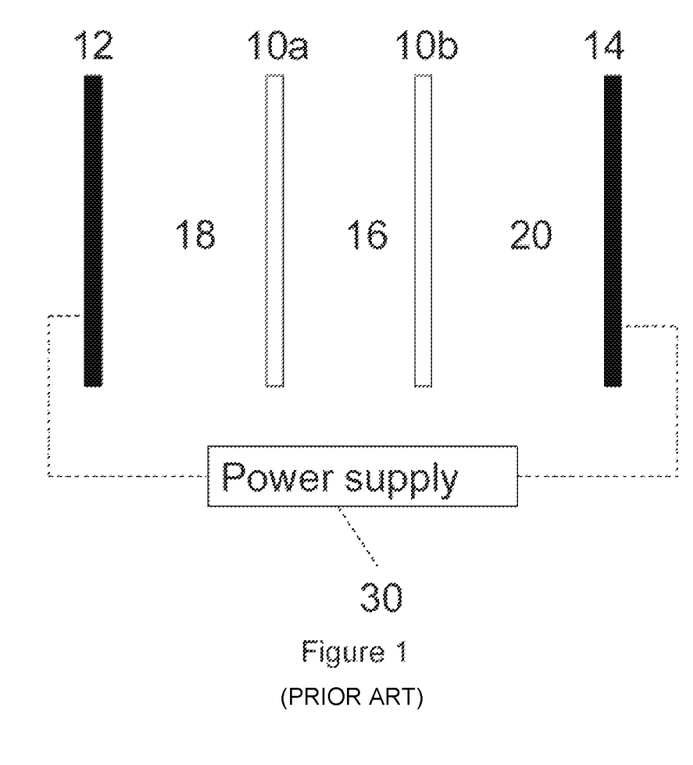
FIG. 1 is a schematic view of a prior art electrolytic suppressor.

FIG. 1 illustrates a membrane suppressor design of the prior art and as described in detail in the '434 patent relating to FIGS. 1-4. Two ion exchange membranes (barriers) 10a and 10b defined three channels. The central channel 16 is the sample stream flow channel and the side channels 18 and 20 flanking the two barriers are regenerant (ion source and receiving) channels, respectively. Electrodes 12 and 14 are disposed in the regenerant channels and extend co-extensively therewith to serve as anode and cathode, respectively. A power supply 30, is in electrical communication with electrodes 12 and 14, is configured to supply a current and potential across the electrodes. For anion analysis, the membranes 10a and 10b are cation exchange membranes. The electrodes 12 and 14 are an anode and a cathode, respectively. Channels 16, 18, and 20 can be filled with cation exchange medium such as ion exchange screens or a packed bed of ion exchange particles. In operation, when an eluent is pumped into the sample stream flow channel and an aqueous stream is supplied to flow channels 18 and 20 and a potential exceeding approximately 1.5 V is applied across electrodes 12 and 14, an electrolytic water splitting reaction occurs resulting in formation of hydronium ion at the anode 12, while hydroxide ion is formed at the cathode 14. The cations (counterions to the anion analyte ions) are transported across the whole device across the anion exchange barriers from the anode to the cathode. This process drives the hydronium ion generated at the electrode 12 towards the cathode electrode 14. This migration process also facilitates the exchange of the sodium ions from the eluent with hydronium ions and the conductive sodium carbonate eluent is converted to a weakly dissociated carbonic acid form. The analytes are fully dissociated. For example, sodium chloride is converted to a conductive hydrochloric acid form. The effluent from channel 16 is routed to a suitable detector (not shown) such as a conductivity detector for detection and quantitation. A suitable current is applied based on equation (1) so that the eluent can be suppressed completely. In operation the entire current that is applied is distributed across the entire electrode surface 12 and 14. The device of the prior art with carbonate eluent would yield a peak to peak noise of greater than 3 nS/cm. It should be noted that the noise would be higher at a higher eluent concentration.

Figure 2:
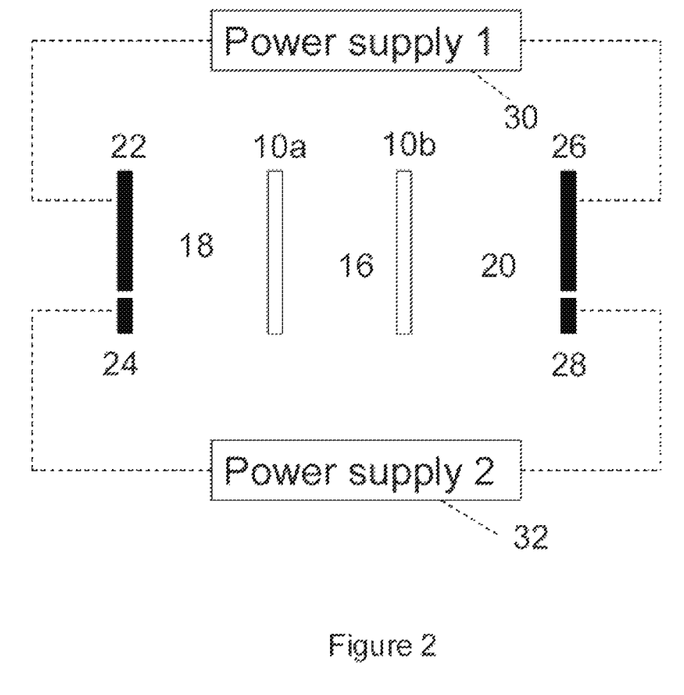
FIG. 2 and FIG. 3 are different embodiments of an electrolytic suppressor for performing the method of the present invention.

One device of the present invention is shown FIG. 2. The device comprises of two ion exchange membrane barriers 10a and 10b defining three channels 16, 18 and 20 as previously described for FIG. 1. In the present invention all components are similar to that of FIG. 1 except the electrode 22 and 26 are shorter than the electrodes 12 and 14. Two additional electrodes 24 and 28 are configured on the downstream portion of the eluent screen and positioned in such a way that there is no physical communication between the electrodes 24 and 28 and the electrodes 22 and 26. This can be achieved by spacing a small gap between the electrodes as shown by the gap between 22 and 24. The electrodes 22 and 26 are powered by a first power supply. Electrodes 24 and 28 are powered by a second power supply 32.

According to the present invention, the current applied to the second power supply is always lower than the current applied to the first power supply. The net effect of the lower current across the electrodes 24 and 28 is lower noise, and the peak to peak noise of a sodium carbonate eluent is in the <1 nS/cm regime, as opposed to 3 to 5 nS/cm for the suppressor of the prior art. In operation in a preferred embodiment, the current applied across the electrodes 22 and 26 is used for completely suppressing the eluent. The current per unit area of that electrode pair is higher than devices of the prior art, since the electrode area is smaller. The current applied across the electrodes 24 and 28 is used for minimizing the variation in the suppressed eluent such as carbonic acid effluent in the eluent channel, thus effecting lower noise. Applying a current across electrodes 24 and 28 ensures that the device is regenerated and preserves the suppression function. Also, during system startup after shut-down, powering the electrodes ensures the outlet portion of the device is free of eluent counterions. If the outlet of the suppressor is in the eluent counterion form, the suppressor function is not maintained and the analytes could be converted to the eluent or sample counterion form rather than the suppressed acid or base form.

Figure 3:
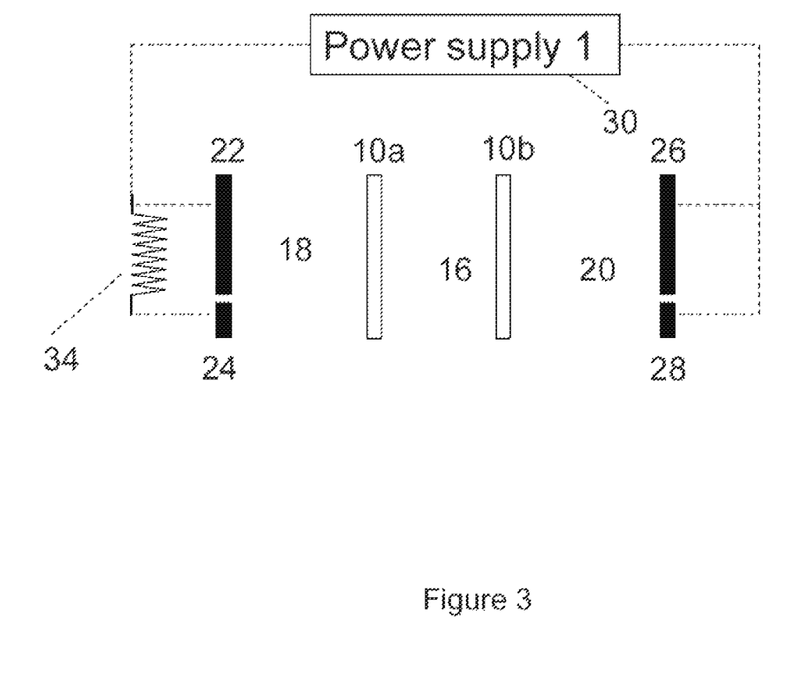

FIG. 3 shows another embodiment of the present invention where all parts are similar to FIG. 2 except a resistor 34 is connected in series across the electrodes 22 and 24. In this setup there is no need for a second power supply, and the power supply 30 is sufficient to achieve the low noise performance of the present invention. The benefits of this design are lower cost and permitting the suppressor to be used with existing instrumentation. The resistor is chosen so that the applied current is divided between the upstream electrodes 22 and 26 and the downstream electrodes 24 and 28. Due to the resistor 34, the current applied to the downstream electrodes is always lower than the upstream electrodes. The current applied to the downstream electrode can be adjusted by adjusting the resistor 34. The total current can be adjusted by tuning the current applied by the power supply 30. Due to the low currents generated in this design the wattage across the resistor is very low.

The resistor 34 has a resistance of greater than 100 ohms, but preferably less than 2000 ohms, more preferably less than 1000 ohms, and most preferably less than 600 ohms The resistor is chosen so that the current applied to the downstream electrodes is roughly less than 25% of the current applied across the upstream electrodes, more preferably less than 10% of the current applied across the upstream electrodes, and most preferably less than 5% of the current applied across the upstream electrodes, but at least 1% of that current applied. The wattage across the resistor 34 is preferably below 1 watt, more preferably below 0.1 watt, and most preferably below 0.01 watt, but at least 0.0001 watt. The lower wattage ensures minimal heat generation in the device of the present invention.

The magnitude of the current in the upstream portion for a 4 mm suppressor operating at 1 ml/min suitably is from 0.1 to 300 mA, preferably from 1 to 200 mA and most preferably from 5 to 150 mA. The magnitude of the current in the downstream portion suitably is from 0.01 to 30 mA, preferably from 0.5 to 5 and most preferably from 1 to 3 mA. For other format suppressors such as a 2 mm suppressor the operational flow rate is four fold lower at 0.25 ml/min and the applied current would also be four-fold lower. Note the operational flow rate for a given column id. can be calculated based on the ratio of the square of the internal diameter of the column. Optimal flow rate for a 4 mm format is 1 ml/min and therefore for the 2 mm format the optimal flow rate or operational flow rate is calculated as 0.25 mL/min.

The gap between the upstream and downstream electrodes is preferably below 0.4 inch, more preferably below 0.2 inch, and most preferably below 0.1 inch, but preferably at least 0.05 inch. The gap ensures that there is no direct electrical communication between the upstream and downstream electrodes. The upstream versus downstream electrode length can be chosen so that suppression is preferably near completion in the upstream portion of the suppressor. A typical ratio of downstream electrode length to the upstream electrode length is preferably less than 0.5 and more preferably less than 0.3. Similarly, the typical ratio of downstream electrode area to the upstream electrode area is preferably less than 0.5 and more preferably less than 0.3. A typical total electrode area is approximately 6 square cm for the anode and cathode respectively.

Figure 4:
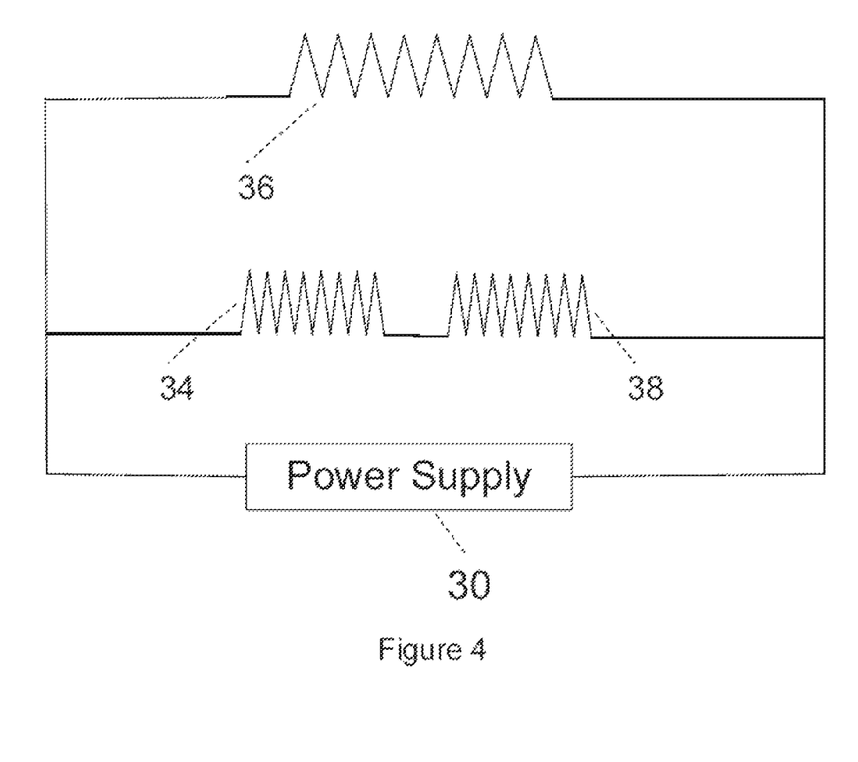
FIG. 4 illustrates a resistor diagram for the electrolytic suppressor of FIG. 3.

FIG. 4 shows a resistor diagram of the arrangement in FIG. 3. The resistor 36 is the resistance across the upstream electrodes while the resistor 38 is the resistance across the downstream electrodes. The resistor 34 is a fixed resistor in this example. In an alternate embodiment, the resistor 34 can be a variable resistor which can be used to change the current applied across the resistor 38. The applied current from the power supply 30 can be divided across the upstream and downstream electrodes. It should be noted that while constant current is preferred, a constant voltage or power could be used to achieve the conditions of the present invention. The preferred current ratio of the downstream current to the upstream current is preferably less than 0.5, more preferably less than 0.3 and most preferably less than 0.1. Thus the downstream current is always lower than the upstream current as per the present invention. This configuration lowers the amount of gas in the regenerant channels at the downstream portion and results in low noise.

In another embodiment, not shown, the electrode 26 and 28 can be combined to form a single electrode while keeping a gap between the electrodes 22 and 24. It should be also noted that the location of the resistor could be changed to across 26 and 28 if needed to achieve the same results of low current across the downstream electrodes relative to the upstream electrodes. Similarly an additional resistor can be used across electrodes 26 and 28. Thus various means of achieving a lower current on the downstream electrodes are possible as per the present invention.

While continuous operation is preferred in the above embodiments, the current applied to the downstream electrodes could be in an intermittent fashion thus having no or low current during the chromatographic run but turning on the current to higher value in an intermittent fashion.

Figure 5:
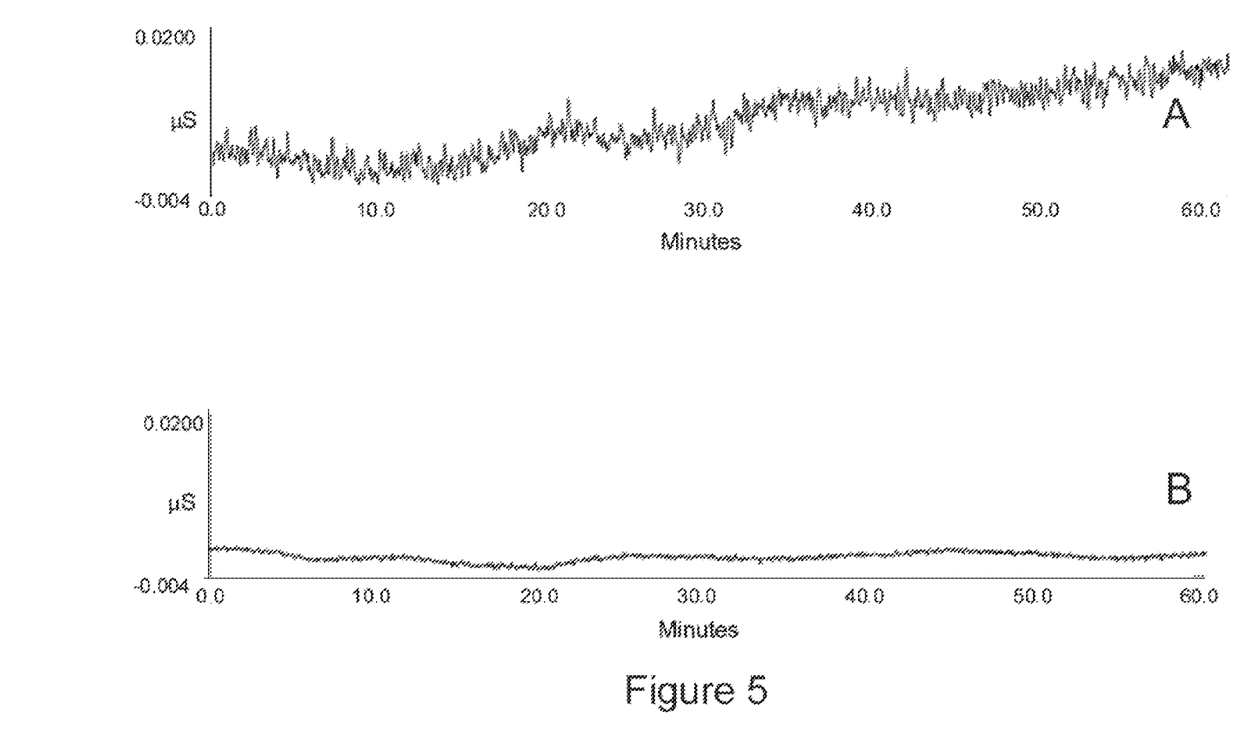
FIG. 5A illustrates experimental results using a prior art method.
FIG. 5B illustrates experimental results using the method of the present invention.
Figure 6:
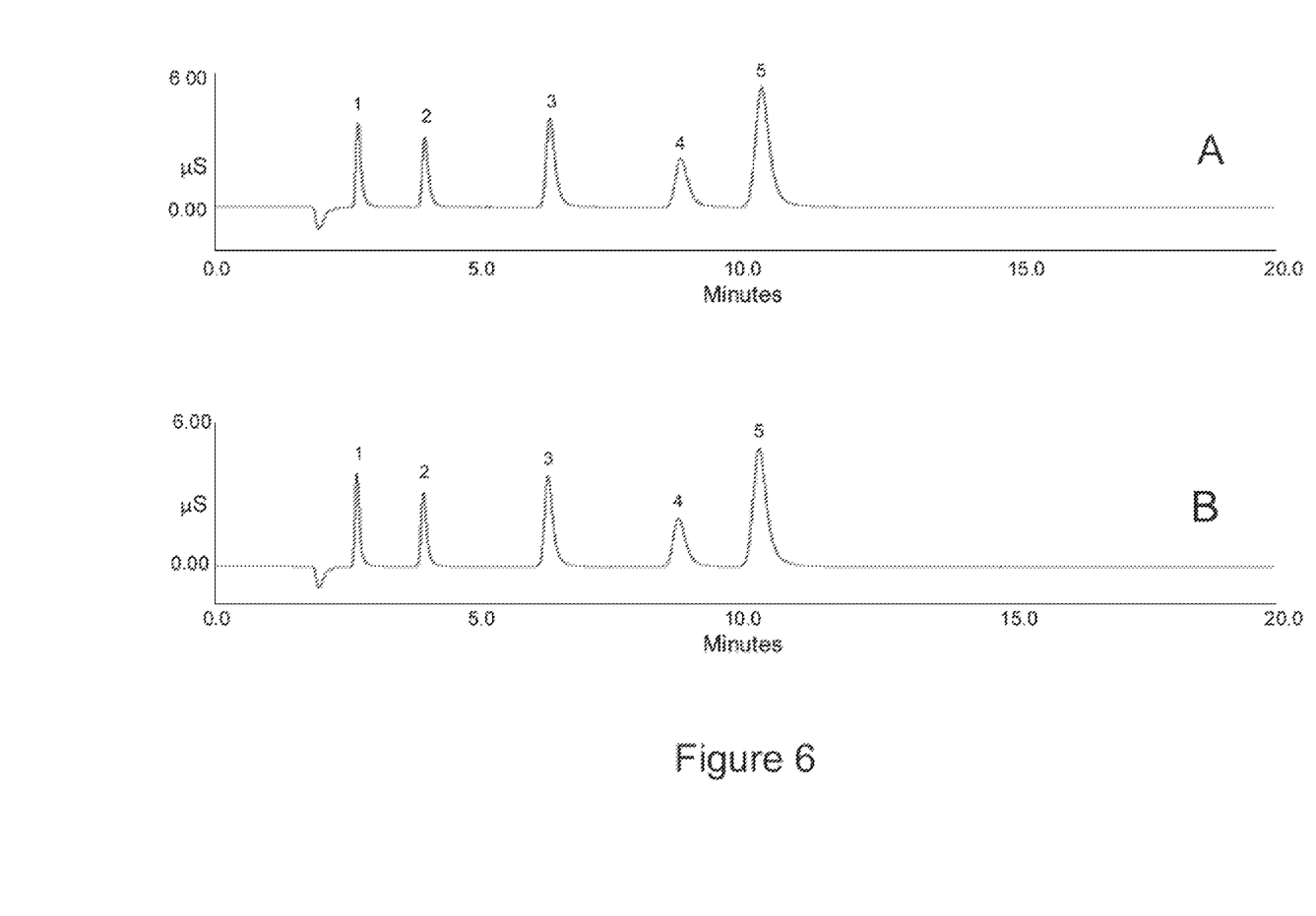
FIG. 6A illustrates experimental results using a prior art method.
FIG. 6B illustrates experimental results using the method of the present invention.

It should be noted that while the above discussion pertains to a three channel device, the invention applies to a single ion exchange barrier-based, two-channel suppressor device such as described with respect to FIG. 5 and FIG. 6 of the '434 patent. Similarly, a multi-channel device would benefit from the present invention by applying a reduced current on a pair of downstream electrodes that are electrically communicating across the channel that is upstream from a detector.

In order to illustrate the present invention, the following non-limiting examples of its practice are provided.

EXAMPLE 1

An anion suppressor was assembled following the schematic of FIG. 2. The suppressor was assembled with two cation exchange membranes 10a and 10b. The regenerant channels 18 and 20 had ion exchange screens placed in them. The eluent channel 16 had cation exchange resin which was polystyrene DVB based and 16% crosslinked and sulfonated. The suppressor device was assembled with four electrodes 22-28, and powered using a DC power supply. The performance of this suppressor was compared to the performance of a prior art commercial suppressor. A Thermo Scientific Dionex ICS-3000 and Thermo Scientific Dionex ICS-2000 ion chromatograph system were used in this work. A 4×250-mm IonPac AS22 column was used for the analysis, using an eluent comprised of 4.5 mM sodium carbonate and 1.4 mM sodium bicarbonate at a flow rate of 1.2 mL/min. The prior art commercial suppressor was run with a power supply providing a constant current of 31 mA and 45 mA respectively, and the four electrode suppressor was run with a power supply providing a constant current of 42 mA on the first set of electrodes, and a separate power supply providing a constant current of 3 mA on the second downstream set of electrodes. The four electrode suppressor showed a noise of 0.75 nS/cm versus 4.7 nS/cm at 31 mA and 6.02 nS/cm at 45 mA (data not shown) for the prior art commercial suppressor. FIGS. 5A and 5B compare the noise performance of the two suppressors. The prior art commercial suppressor noise performance at constant current of 31 mA is shown in FIG. 5A and the four electrode suppressor device noise performance is shown in FIG. 5B. The results indicated a significant decrease in baseline noise using the four electrode suppressor of the present invention.

EXAMPLE 2

A test mixture comprised of five anions was analyzed using the four electrode suppressor. FIGS. 6A and 6B show the chromatograms obtained on a 4×250-mm IonPac AS22 column, with an eluent concentration of 4.5 mM sodium carbonate and 1.4 mM sodium bicarbonate at a flow rate of 1.2 mL/min. The sample comprised of Fluoride at 2.0 mg/L (Peak 1), Chloride at 3.0 mg/L (Peak 2), Nitrate at 10.0 mg/L (Peak 3), Phosphate at 15.0 mg/L (Peak 4), and Sulfate at 15.0 mg/L (Peak 5). The prior art commercial suppressor was run at a constant current of 31 mA (FIG. 6A) and the four electrode suppressor was run at a constant current of 42 mA, with a 500Ω resistor inline prior to the second electrode on the cathode side (FIG. 6B). The results indicated excellent performance of the four electrode suppressor device. The results also indicated comparable performance to the prior art commercial suppressor in terms of efficiency, peak shapes and peak response. The peak to peak noise continued to remain low using the four electrode suppressor device.

EXAMPLE 3

Figure 7:
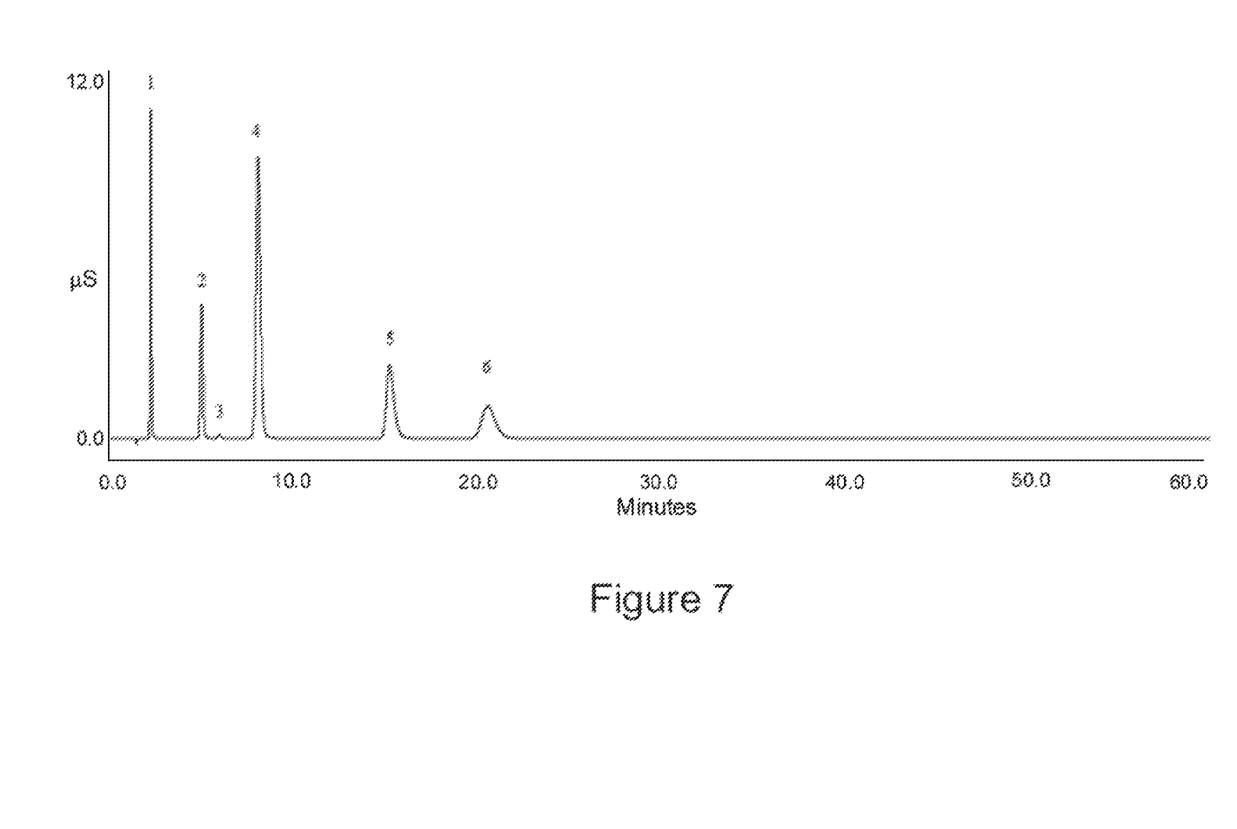
FIG. 7 illustrates experimental results using the method of the present invention.

This example shows the analysis of five inorganic anions using a 4×250-mm IonPac AS15 column, with an eluent comprising of 38 mM potassium hydroxide at a flow rate of 1.2 mL/min. The first set of electrodes were powered with one power supply providing a constant current of 113 mA, and the second set of electrodes were powered by a separate power supply providing a constant current of 3 mA. A Thermo Scientific Dionex ICS-3000 system was used in this work. FIG. 7 shows the chromatogram obtained with this set up, with the a sample comprising of Fluoride at 2.0 mg/L (Peak 1), Chloride at 3.0 mg/L (Peak 2), Carbonate (not quantified) (Peak 3), Sulfate at 15.0 mg/L (Peak 4), Nitrate at 10.0 mg/L (Peak 5), and Phosphate at 15.0 mg/L (Peak 6). Excellent peak shape can be inferred from this work. The peak to peak noise was 0.71 nS/cm, which is low.

EXAMPLE 4

Figure 8:
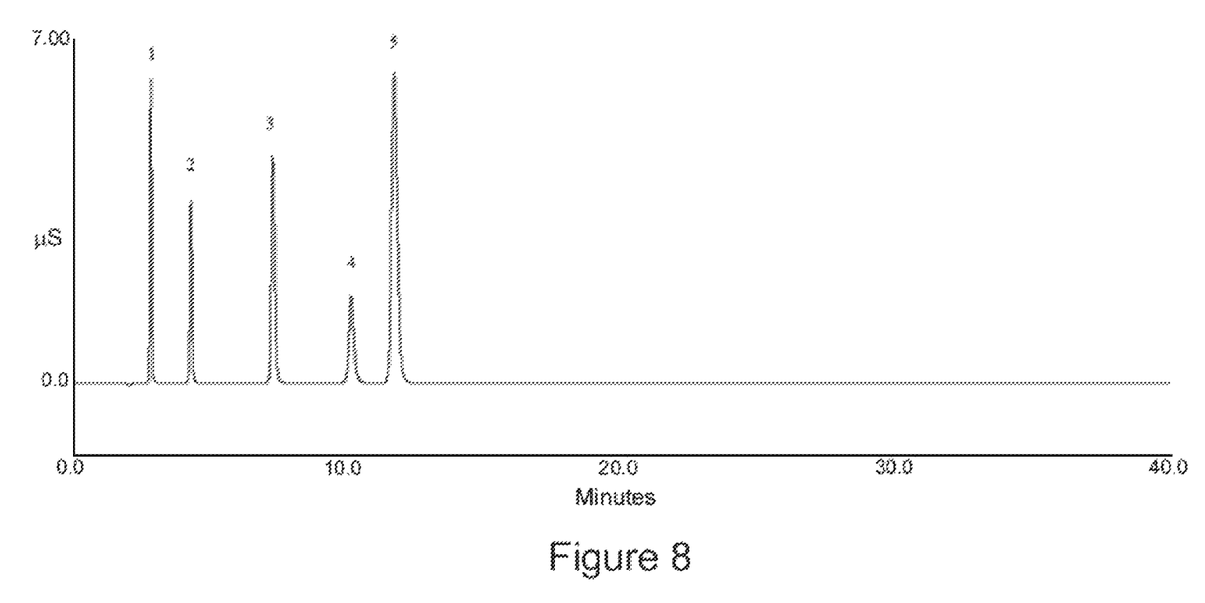
FIG. 8 illustrates experimental results using the method of the present invention.

This example shows the analysis of five inorganic anions using a 4×250-mm AS22 column, with an eluent concentration of 4.5 mM sodium carbonate and 1.4 mM sodium bicarbonate at a flow rate of 1.2 mL/min, in conjunction with a Thermo Fisher Dionex CRD 300 carbonate removal device using 200 mM sodium hydroxide as the regenerant solution. A Thermo Scientific Dionex ICS-3000 system was used in this work. FIG. 8 shows the chromatogram obtained with this setup, using a sample comprising of Fluoride at 2.0 mg/L (Peak 1), Chloride at 3.0 mg/L (Peak 2), Nitrate at 10.0 mg/L (Peak 3), Phosphate at 15.0 mg/L (Peak 4), and Sulfate at 15.0 mg/L (Peak 5), with the suppressor in the split flow recycle mode. The suppressor was run with a power supply providing a constant current of 42 mA to the first set of electrodes, and a separate power supply providing a constant current of 3 mA to the second set of electrodes. The peak to peak noise was 0.27 nS/cm which is extremely low; using a standard suppressor, the noise was roughly 3× higher. Thus, the device of the present invention offers excellent noise performance.

What is claimed is:

1. An electrolytic method for suppressing liquid eluent containing previously separated sample analyte anions, counterions to said sample anions, and non-sample anions suppressible to weak acids; using an electrolytic device comprising a housing defining at least a sample stream flow channel and an ion receiving flow-through channel, said sample stream flow channel being adjacent to said ion receiving flow channel; a first ion exchange barrier which permits ion transport and blocks bulk liquid flow disposed between said sample stream flow channel and said ion receiving flow channel, said sample stream flow channel including an upstream channel portion and a downstream channel portion; and high capacity ion exchange medium disposed in said downstream channel portion; said method comprising applying a first current across said upstream channel portion to substantially completely suppress said counterions and to convert said non-sample anions to weak acids in said upstream channel portion by transport of said counterion across said first ion exchange barrier; applying a second current across said downstream channel portion to substantially reduce the noise of said weak acids during subsequent detection, said second current being at a magnitude of less than 10% of the magnitude of said first current.

2. The method of claim 1 in which the magnitude of said first current is from 0.1 to 300 mA.

3. The method of claim 1 in which the magnitude of said second current is from 0.01 to 30 mA.

4. The method of claim 1 in which said weak acid anions comprise carbonate, bicarbonate or borate anions.

5. The method of claim 1, in which said first current is applied by first and second electrodes.

6. The method of claim 1 in which said second current is applied by third and fourth electrodes.

7. The method of claim 1 in which said first current is applied by first and second electrodes; said second current is applied by third and fourth electrodes, and said first and third electrodes are operatively connected.

* * * * *